(12) United States Patent
Rigler et al.

(10) Patent No.: US 7,553,620 B2
(45) Date of Patent: Jun. 30, 2009

(54) METHOD FOR DETERMINING POLYNUCLEOTIDES IN A SAMPLE WITHOUT ATTACHING THESE TO A SUPPORT, AND USING DETECTION PROBES

(75) Inventors: Rudolf Rigler, St-Sulpice (CH); Zeno Foldes-Papp, Graz (AT)

(73) Assignee: Gnothis Holdings S.A., Ecublens (CH)

( * ) Notice: Subject to any disclaimer, the term of this patent is extended or adjusted under 35 U.S.C. 154(b) by 180 days.

(21) Appl. No.: 10/276,039

(22) PCT Filed: May 11, 2001

(86) PCT No.: PCT/EP01/05410

§ 371 (c)(1),
(2), (4) Date: Mar. 26, 2003

(87) PCT Pub. No.: WO01/85991

PCT Pub. Date: Nov. 15, 2001

(65) Prior Publication Data

US 2003/0165929 A1 Sep. 4, 2003

(30) Foreign Application Priority Data

May 12, 2000 (DE) .............................. 100 23 421
Dec. 29, 2000 (DE) .............................. 100 65 632

(51) Int. Cl.
*C12Q 1/68* (2006.01)
(52) U.S. Cl. ......................................................... 435/6
(58) Field of Classification Search ...................... 435/6, 435/287.2
See application file for complete search history.

(56) References Cited

U.S. PATENT DOCUMENTS

| 6,023,540 | A | | 2/2000 | Walt et al. |
| 6,133,436 | A | * | 10/2000 | Koster et al. ............... 536/24.3 |
| 6,297,062 | B1 | * | 10/2001 | Gombinski .................. 436/526 |
| 6,406,848 | B1 | * | 6/2002 | Bridgham et al. .............. 435/6 |
| 6,429,027 | B1 | * | 8/2002 | Chee et al. ................... 436/518 |
| 6,582,903 | B1 | * | 6/2003 | Rigler et al. .................... 435/6 |
| 6,858,394 | B1 | * | 2/2005 | Chee et al. ................... 435/7.1 |
| 6,887,431 | B1 | * | 5/2005 | Vann et al. ................... 422/100 |
| 2003/0082587 | A1 | * | 5/2003 | Seul et al. ....................... 435/6 |

FOREIGN PATENT DOCUMENTS

| EP | 0-679 251 A | | 7/1994 |
| WO | 94/16313 | * | 7/1994 |
| WO | WO-97 14028 A | | 4/1997 |
| WO | WO-01 00875 A | | 1/2001 |
| WO | WO-01 14589 A | | 3/2001 |

OTHER PUBLICATIONS

Rigler, et al., Fluorescence cross-correlation: A new concept for polymerase chain reaction, Journal of Biotechnology, Elsevier Science Pub. B.V. No. 2, Aug. 12, 1998.

* cited by examiner

*Primary Examiner*—Kenneth R. Horlick
(74) *Attorney, Agent, or Firm*—Fulbright & Jaworski LLP

(57) ABSTRACT

The invention relates to a method for detecting polynucleotides on a substrate, whereby the substrate contains a multitude of separate detection regions each accommodating different polynucleotides. The polynucleotides in the detection regions exist, contrary to known DNA chip test formats, in a form that is not bound to the substrate. The invention also relates to a device for implementing said method.

15 Claims, 2 Drawing Sheets

METHOD FOR DETERMINING POLYNUCLEOTIDES IN A SAMPLE WITHOUT ATTACHING THESE TO A SUPPORT, AND USING DETECTION PROBES

The invention relates to a method for detecting polynucleotides on a support which contains a multiplicity of separate detection regions with in each case different polynucleotides. In contrast to known DNA-chip test formats, the polynucleotides in said detection regions are not bound to said support. Furthermore, an apparatus for carrying out the method is disclosed.

The use of "DNA chips" for determining polynucleotides is known (see, for example, European patents EP 0 373 203 and 0 619 321). DNA chips of the prior art contain a multiplicity of separate detection regions on the surface of a support, which contain in each case different polynucleotides in a support-bound form. However, these DNA chips have a disadvantage in that the reactivity of the polynucleotides immobilized on the support differs substantially from the reactivity of free polynucleotides, as are present in biological systems. This leads to fundamental problems when evaluating hybridization experiments using common DNA chips.

It was the object of the present invention to provide novel methods for determining polynucleotides, whose efficiency, on the one hand, is comparable to that of common DNA chips but which, on the other hand, eliminate the disadvantages which the use of immobilized polynucleotides entails.

This object is achieved by a method for determining polynucleotides, comprising the steps:
(i) providing /a support containing a plurality of separate detection regions each of which contains a polynucleotide which is not bound to said support,
(ii) contacting the polynucleotides located in said detection regions with detection probes, with individual detection regions each containing different combinations of polynucleotide and detection probe, and
(iii) determining a hybridization of said polynucleotides with said detection probes.

A substantial advantage of the method of the invention is the possibility of hybridizing the polynucleotides to be studied with detection probes in very small measuring volumes and at very low concentrations of the reaction partners. To this end, preference is given to using the method of fluorescence correlation spectroscopy (FCS) described in European patent 0 679 251 or another fluorescence spectroscopy method with sufficient sensitivity. Said FCS preferably comprises measuring one or a few sample molecules in a measuring volume, the concentration of the molecules to be determined being $\leq 10^{-6}$ mol/l and the measuring volume being preferably $\leq 10^{-14}$ l. Fluorescence correlation spectroscopy comprises determining substance-specific parameters which are obtained by luminescence measurements on the molecules to be determined. These parameters may be translational diffusion coefficients, rotational diffusion coefficients or/and the excitation wavelengths, the emission wavelengths or/and the lifetime of an excited state of a luminescent substituent or the combination of said parameters. For details of carrying out the method and details of the apparatuses used for said method, reference is made to the disclosure of European patent 0 679 251.

As an alternative, it is also possible to carry out a fluorescence decay measurement in which the relaxation time of the fluorescent label or the occurrence of energy transfer or quenching processes is determined.

The polynucleotides arranged in the detection regions of the support are preferably nucleic acids such as DNA or RNA, DNA polynucleotides being particularly preferred. On the other hand, it is also possible to use nucleic acid analogs such as, for example, peptide nucleic acids (PNA) as polynucleotides. On the one hand, the polynucleotides may be derived from natural resources, for example from gene or cDNA libraries and may be genes, cDNA molecules or fragments thereof but, on the other hand, they may also be synthetically generated, for example combinatorial, polynucleotide sequences. The polynucleotides are in a form which can hybridize with a complementary detection probe under the conditions of the detection method. The polynucleotides are preferably single-stranded.

Preferably the support contains a plurality of detection regions each of which contains a polynucleotide with differing sequence. However, it is also possible to use a support having a plurality of detection regions which in each case contain a polynucleotide with identical sequence. In this case, a different detection probe must be employed for each of these detection regions. The length of the polynucleotides in the detection regions is preferably at least 10 nucleotides to several thousand nucleotides.

The detection probes used for studying a hybridization with the polynucleotides located in the detection regions may, like the polynucleotides themselves, be derived from natural or synthetic sources. The detection probes preferably carry one or more labeling groups which may be introduced during synthesis of the detection probes (in particular in chemical synthesis or in amplification) or else after synthesis of the detection probes (for example via enzymatic attachment to the 5' or 3' end). Thus it is possible to generate labeled detection probes, for example, via reverse transcription of RNA molecules, for example of mRNA molecules, by using labeled primers or via enzymatic primer extension by using labeled nucleotide building blocks.

In a particularly preferred embodiment of the invention, polynucleotides coupled to a microparticle are used. The size of said microparticle is sufficient for slowing down the rate of diffusion of a polynucleotide coupled thereto. On the other hand, however, the microparticle is also sufficiently small in order to ensure that the reaction behavior of the polynucleotide coupled thereto essentially corresponds to that of a "free" but not an "immobilized" polynucleotide. The microparticle size is preferably $\leq 1$ μm, particularly preferably 10 nm to 500 nm. The microparticles may be latex particles, for example of polystyrene, or other polymers, metal sol particles, silica particles, quartz particles or glass particles. Polynucleotides can bind to microparticles via covalent or noncovalent interactions. For example, binding of the polynucleotide to the microparticle can be mediated by high-affinity interactions between the partners of a specific binding pair, for example biotin/streptavidin or avidin, hapten/anti-hapten antibody, sugar/lectin, etc. Thus it is possible to couple biotinylated polynucleotides to streptavidin-coated microparticles. As an alternative, it is also possible to bind the polynucleotides to particles via adsorption. Thus it is possible to bind polynucleotides modified by incorporation of alkanethiol groups to metal particles, for example gold particles. Yet another alternative is covalent immobilization in which binding of the polynucleotides can be mediated via reactive silane groups on a silica surface. It is also possible, where appropriate, to use alternatively or additionally detection probes coupled to microparticles.

A further possibility is to prepare the polynucleotides or detection probes by support-based synthesis on the particle by using known solid-phase synthesis methods.

A single polynucleotide strand may be bound to a microparticle. However, it is also possible to bind a plurality of, for example, up to several thousand, polynucleotide strands to a particle. Binding takes place preferably via the 5' or the 3' terminals of the polynucleotide strand.

The method of the invention uses a support with a plurality of, preferably with a multiplicity of $10^2$ or more, separate detection regions. The detection regions are designed in such a way that they enable hybridization of the polynucleotide with the detection probe in solution. The detection regions are preferably depressions in the support surface, it being in principle possible for said depressions to have any shape, for example circular, square, diamond-shaped, etc. The volume of the detection regions is preferably $\leq 10^{-6}$ l and particularly preferably $\leq 10^{-8}$ l. The support preferably contains $10^3$ or more, particularly preferably $10^4$ or more, separate detection regions.

Preferred concentrations of the polynucleotides to be determined in the detection regions are $\leq 10^{-6}$ mol/l, particularly preferably $10^{-10}$ to $10^{-14}$ mol/l, while the detection probes are supplied at a concentration of preferably $\leq 10^{-4}$ mol/l, particularly preferably $10^{-8}$ mol/l to $10^{-11}$ mol/l.

The method of the invention preferably uses labeled detection probes, labels detectable via luminescence measurements, in particular labels detectable via fluorescence measurement, being preferred. When the detection probe used in a detection region hybridizes with the polynucleotide located there, this hybridization causes a detectable change in a substance-specific parameter. This detectable change can be measured via fluorescence measurement. Thus, for example, in the case of hybridization of detection probe and polynucleotide, the mobility of the hybrid is detectably reduced compared with the starting components. As an alternative or in addition, it is also possible to detect the occurrence of quenching processes or energy transfer processes during hybridization. Such energy transfer processes occur, for example, when using a plurality of different labeled probes or labeled polynucleotides and labeled probes.

Thus, for example, detection may be carried out by means of confocal single-molecule detection, for example via fluorescence correlation spectroscopy according to EP 0 679 251, for which a very small, preferably confocal, volume element, for example from $0.1 \times 10^{-15}$ to $20 \times 10^{-12}$ l, is exposed to the excitation light of a laser, which excites the fluorescently labeled detection probes located in this measuring volume so that they emit fluorescence light, the emitted fluorescence light being measured by means of a photodetector and a correlation being determined between the change in the measured emission with time and the mobility of the fluorescent labeling group. The confocal determination of single molecules is furthermore described in Rigler and Mets (Soc. Photo-Opt. Instrum. Eng. 1921 (1993), 239 ff.) and Mets and Rigler (J. Fluoresc. 4 (1994), 259-264).

As an alternative or in addition, detection may also be carried out via time-resolved decay measurement, so-called time gating, as described, for example, by Rigler et al.: Picosecond Single Photon Fluorescence Spectroscopy of Nucleic Acids, in: "Ultrafast Phenomena", D. H. Auston ed. Springer 1984. In this case, the fluorescent molecules are excited in a measuring volume followed by, preferably at a time interval of $\geq 100$ ps, opening a detection interval on the photodetector. In this way it is possible to keep background signals generated by Raman effects sufficiently low so as to make possible an essentially interference-free detection. Time gating is particularly suitable for measuring quenching processes or energy transfer processes.

In a preferred embodiment of the method, the determination may also comprise measuring a cross-correlated signal derived from a probe-polynucleotide complex containing at least two different labels, in particular fluorescent labels, it being possible to use a plurality of differently labeled probes or/and polynucleotides with in each case different labels. This cross-correlation determination is described, for example, in Schwille et al. (Biophys. J. 72 (1997), 1878-1886) and Rigler et al. (J. Biotechnol. 63 (1998), 97-109).

The support used for the method should be designed so as to make possible optical detection in the detection regions. Therefore preference is given to using a support which is optically transparent at least in said detection regions. The support may either have total optical transparency or contain an optically transparent base and an optically impermeable cover layer with gaps in the detection regions. Examples of materials suitable for supports are composite supports made from metal (e.g. silicon for the cover layer) and glass (for the base). Supports of this type can be generated, for example, by applying a metal layer with predetermined gaps for the detection regions to the glass. As an alternative, it is possible to use plastic supports, for example of polystyrene, or polymers based on acrylate or methacrylate.

The invention further relates to an apparatus for determining polynucleotides, comprising a support containing a plurality of separate detection regions each of which contains a polynucleotide which is not bound to the support. The apparatus may be prepared by introducing the polynucleotides into the detection regions of the support in the form of a solution, preferably an aqueous solution, and subsequent drying. The apparatus generated in this way is stable for a long time, for example several months.

The invention still further relates to a kit of reagents for determining polynucleotides, comprising a device of the invention and (a) a set of labeled detection probes or (b) means for preparing a set of labeled detection probes, for example labeled primers or labeled (deoxy)ribonucleoside triphosphates, and, where appropriate, enzymes for preparing suitable detection probes.

The method of the invention may be used, for example, for functional genomics and for transcriptome analysis.

BRIEF DESCRIPTION OF THE FIGURES

Furthermore, the present invention is intended to be illustrated by the following figures and examples in which.

Figure 1:
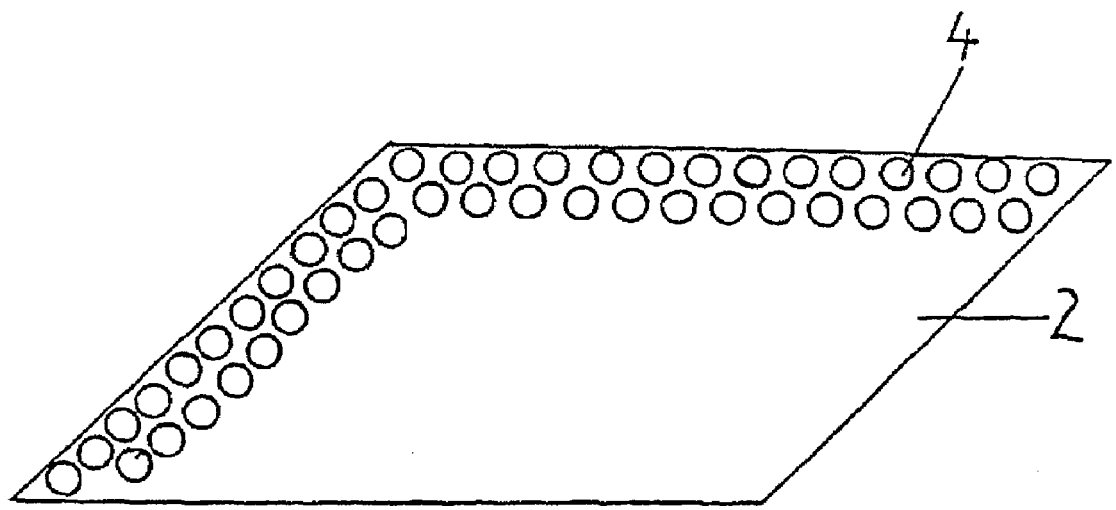
FIG. 1: shows the diagrammatic representation of a support (2) suitable for carrying out the method of the invention, having a multiplicity of detection regions (4) formed as depressions on said support. A support having an area of from 1 to 2 cm$^2$ may contain, for example, up to $10^4$ depressions.
Figure 2:
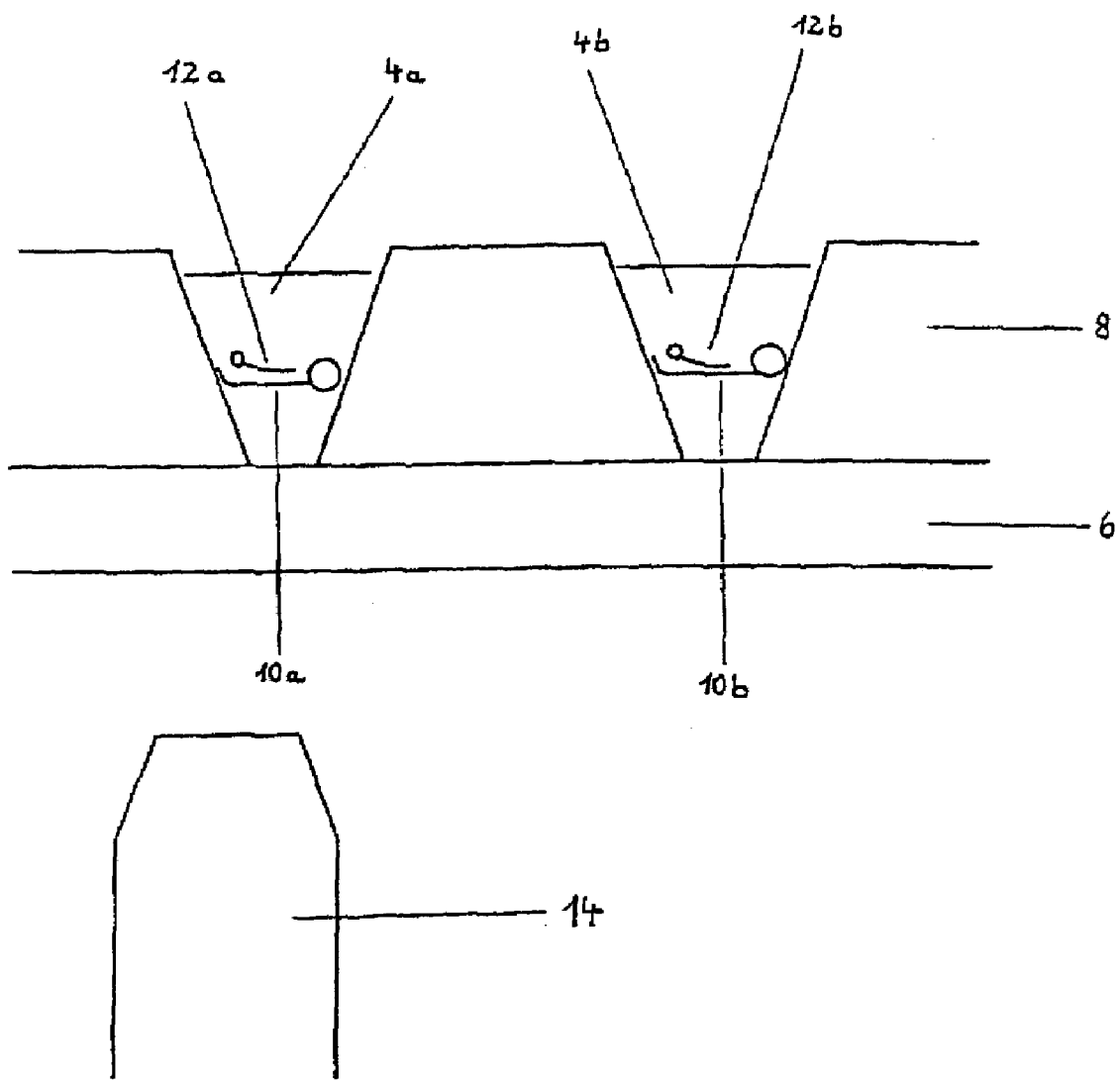
FIG. 2: shows a cross section through a support of the invention. The support contains a base (6), preferably made from an optically transparent material such as glass, and a cover layer (8) with gaps, for example made from silicon. Two detection regions (4a, 4b) are shown which contain in each case a polynucleotide (10a, 10b) coupled to a microparticle and a detection probe (12a, 12b). In the detection region (4a) the polynucleotide (10a) hybridizes with the detection probe (12a), while in the detection region (4b) no hybridization between the polynucleotide (10b) and the detection probe (12b) takes place. A hybridization between microparticle-coupled polynucleotide (10a) and labeled detection probe (12a) can be detected by studying single molecules.

It is possible to use for detection a detection apparatus (14) which is preferably arranged below the support base. The detection apparatus (14) may contain a laser and a detector. Preference is given to using a laser-detector matrix consisting of a dot matrix of laser dots generated by diffraction optics or a quantum well laser and of a detector matrix generated by fiber-coupled individual avalanche photodiode detectors or an avalanche photodiode matrix. Alternatively, it is also possible to use an electronic detector matrix, for example a CCD camera.

DETAILED DESCRIPTION OF THE PREFERRED EMBODIMENTS

EXAMPLE

In a matrix of m×n microdepressions on one or more supports, a library of $4^n$ different nucleotide sequences of length m is generated, and each sequence is transferred to a separate detection region. The nucleotide sequences contain a biotin group on their 5' end and are coupled to streptavidin-coated microparticles.

An mRNA or cDNA library is provided with fluorescently labeled nucleotides at the 3' and/or 5' end by an enzymatic reaction, for example using terminal transferase or ligase. The labeled nucleotides are pipetted into the depressions of the support.

Specific hybridization between polynucleotide and a labeled detection probe is carried out by analyzing the translation movement using confocal single-molecule analysis. Detection is carried out via a laser detector matrix.

The invention claimed is:

1. A method for determining a target polynucleotide, comprising:
   providing a support containing a plurality of separate detection regions, each of which contains a target polynucleotide to be determined which is neither directly nor indirectly bound to said support;
   contacting the target polynucleotide located in each of said detection regions with a labeled detection probe, with individual detection regions each containing different combinations of hybridizing target polynucleotide and labeled detection probe to form hybrid molecules between said target polynucleotide and said labeled detection probe; and
   determining hybridization of said target polynucleotide with said labeled detection probe by detecting reduced mobility of hybrid molecules containing target polynucleotide and labeled detection probe, compared with non-hybrid molecules, wherein said target polynucleotide is coupled to a non-immobilized microparticle having a size of $\leq 1$ μm, wherein said non-immobilized microparticle remains in solution during determination of hybridization.

2. The method of claim 1, wherein the polynucleotide concentration in the detection regions is $\leq 10^{-6}$ mol/l.

3. The method of claim 1 wherein the volume of the detection regions is in each case $\leq 10^{-6}$ l or less.

4. The method of claim 1 wherein the support contains at least $10^3$ or more separate detection regions.

5. The method of claim 1, wherein said labeled detection probe is a fluorescent label.

6. The method of claim 1, wherein said determining step is carried out by confocal single-molecule detection.

7. The method of claim 6, wherein said determining step is carried out by at least one method selected from the group consisting of fluorescence correlation spectroscopy and time-resolved decay measurement.

8. The method of claim 1, wherein the determining step comprises detecting the mobility of at least one of said target polynucleotide or said labeled detection probe.

9. The method of claim 1, wherein the determining step comprises detecting the occurrence of quenching processes or energy transfer processes.

10. The method of claim 1, wherein the determining step comprises measuring a cross-correlated signal which is derived from a labeled probe-target polynucleotide complex containing at least 2 different labels.

11. The method of claim 10, wherein said at least two different labels are fluorescent labels.

12. The method of claim 1, wherein said support is optically transparent at least in a detection region.

13. The method of claim 1, wherein said support comprises an optically transparent base and an optically impermeable cover layer with gaps in the detection regions.

14. The method of claim 1, wherein said support comprises at least one material selected from the group consisting of metal, glass and plastic.

15. The method of claim 1, wherein said non-immobilized microparticle has a size of from 10 nm to 500 nm.

* * * * *